(12) United States Patent
Surbur et al.

(10) Patent No.: US 10,588,570 B2
(45) Date of Patent: Mar. 17, 2020

(54) SYSTEM FOR PROVIDING INSIGHTFUL LIFESTYLE NOTIFICATIONS

(71) Applicant: Fitbit, Inc., San Francisco, CA (US)

(72) Inventors: Jacob Aaron Surbur, Redwood City, CA (US); Heather Mehle Shapiro, San Francisco, CA (US); Kevin Thomas Hill, Blacksburg, VA (US)

(73) Assignee: FITBIT, INC., San Francisco, CA (US)

( * ) Notice: Subject to any disclaimer, the term of this patent is extended or adjusted under 35 U.S.C. 154(b) by 0 days.

(21) Appl. No.: 15/699,853

(22) Filed: Sep. 8, 2017

(65) Prior Publication Data

US 2018/0078204 A1 Mar. 22, 2018

Related U.S. Application Data

(63) Continuation of application No. 14/961,668, filed on Dec. 7, 2015, now Pat. No. 9,782,126.

(51) Int. Cl.
| | | |
|---|---|---|
| A61B 5/00 | (2006.01) | |
| G06Q 10/10 | (2012.01) | |
| A61B 5/11 | (2006.01) | |
| G16H 20/70 | (2018.01) | |

(52) U.S. Cl.
CPC ............ *A61B 5/681* (2013.01); *A61B 5/1118* (2013.01); *A61B 5/4806* (2013.01); *G06Q 10/1095* (2013.01); *G16H 20/70* (2018.01); *A61B 2562/0219* (2013.01)

(58) Field of Classification Search
CPC . A61B 5/1118; A61B 2562/0219; A61B 5/48; A61B 5/4806; A61B 5/68; A61B 5/681; G06F 19/00; G06F 19/30; G06Q 10/109; G06Q 10/1095; G16H 20/70

USPC ........... 340/870.01, 870.07, 539.12, 539.22, 340/539.26, 573.1, 575
See application file for complete search history.

(56) References Cited

U.S. PATENT DOCUMENTS

| D733,142 S | 6/2015 | Solomon et al. |
|---|---|---|
| D743,278 S | 11/2015 | Solomon et al. |
| D745,515 S | 12/2015 | Solomon et al. |

(Continued)

FOREIGN PATENT DOCUMENTS

| EP | 2504961 | 10/2012 |
|---|---|---|
| EP | 002655142-0001 | 3/2015 |
| EP | 002655118-0001 | 4/2015 |

OTHER PUBLICATIONS

Fitbit Health App by on Prezi, Prezi FitBit Health Presentation, https://prezi.com/s8sqfrn-fjlr/fitbit-health-app/ downloaded Jun. 9, 2016 from the internet, 3 pages.

(Continued)

*Primary Examiner* — Brian Wilson
(74) *Attorney, Agent, or Firm* — Hogan Lovells US, LLP

(57) ABSTRACT

A lifestyle service with data and routines storable in a memory of a wearable electronic device is discussed. The lifestyle service has at least a Sleep data routine and an Activity data routine. The lifestyle service can cooperate with an insight engine. The lifestyle service is aware of different types of information contained in one or more time synchronous applications. The system can compare tracked physical activity data with historical data in set increments in light of the information in the time synchronous applications and then communicate notifications to the user.

20 Claims, 12 Drawing Sheets

(56) References Cited

U.S. PATENT DOCUMENTS

| | | | |
|---|---|---|---|
| D750,625 S | 3/2016 | Solomon et al. | |
| D752,583 S | 3/2016 | Solomon et al. | |
| D755,178 S | 5/2016 | Solomon et al. | |
| 2005/0250458 A1* | 11/2005 | Graham | G06Q 30/02 455/121 |
| 2008/0275309 A1* | 11/2008 | Stivoric | A61B 5/411 600/300 |
| 2011/0003665 A1 | 1/2011 | Burton et al. | |
| 2013/0040610 A1 | 2/2013 | Migicovsky et al. | |
| 2013/0141235 A1* | 6/2013 | Utter, II | G08B 21/02 340/539.12 |
| 2014/0278229 A1 | 9/2014 | Hong et al. | |
| 2015/0081347 A1 | 3/2015 | Rosenblatt | |
| 2015/0126117 A1 | 5/2015 | Wong et al. | |
| 2015/0223033 A1 | 8/2015 | Migicovsky et al. | |
| 2015/0223034 A1 | 8/2015 | Migicovsky et al. | |
| 2015/0333302 A1 | 11/2015 | Johns et al. | |
| 2015/0334772 A1 | 11/2015 | Wong et al. | |
| 2016/0022203 A1 | 1/2016 | Arnold et al. | |
| 2017/0000348 A1* | 1/2017 | Karsten | G06F 19/3418 |
| 2017/0017776 A1* | 1/2017 | Soulos | G06F 19/3475 |
| 2017/0156666 A1 | 6/2017 | Surbur et al. | |

OTHER PUBLICATIONS

Non-Final Office Action issued in U.S. Appl. No. 14/961,668 dated Mar. 9, 2016.

Final Office Action issued in U.S. Appl. No. 14/961,668 dated Sep. 20, 2016.

Notice of Allowance issued in U.S. Appl. No. 14/961,668 dated May 5, 2017.

\* cited by examiner

SYSTEM FOR PROVIDING INSIGHTFUL LIFESTYLE NOTIFICATIONS

FIELD

The design generally relates to wearable electronics devices for monitoring human lifestyle and providing lifestyle notification.

BACKGROUND

Typically, a wearable electronic device is used as a passive device such as a watch to provide the time, and they do not interact with the lifestyle of the person wearing the device.

SUMMARY

In general, a health service is discussed. The lifestyle service has data and routines storable in a memory in a wearable electronic device in an executable format. A processor in the wearable electronic device can execute the routines of the lifestyle service. The lifestyle service includes at least two routines i) a Sleep data routine and ii) an Activity data routine. The lifestyle service can also cooperate with an insight engine. The Activity data routine can collect and track data on the physical activity of a user of the wearable electronic device. The Activity data routine can cooperate with any of an accelerometer, a magnetometer, a gyroscope, a barometer, a heart rate sensor, and a light sensor, in the wearable electronic device, to collect this data. The Activity data routine can store the tracked physical activity data in the memory of the wearable electronic device. The Activity data routine can cooperate with a graphic user interface to display the tracked physical activity data on a display screen of the wearable electronic device. A Sleep data routine can collect and track sleep data. An insight engine can monitor the tracked sleep data from the Sleep data routine and the tracked physical activity data from the Activity data routine. The Activity data routine can also compare average tracked physical activity data with the tracked physical activity data in set increments that occur at least once per hour.

The insight engine can also monitor one or more time synchronous applications. The insight engine is configured to monitor, by pulling information from or receiving information from, the one or more time synchronous applications. The time synchronous applications include any application that is configured to keep a time synchronized organization of at least two of i) personal communication information, ii) past and future event information, and iii) fact-based information, each of which are logged or scheduled in the one or more time synchronous applications. The applications can be resident either on the wearable electronic device or on a mobile computing device, such as a smart phone such that the mobile computing device can cooperate and communicate with the wearable electronic device.

The insight engine can make correlations based on at least two of 1) the monitored tracked sleep data from the Sleep data routine, 2) the monitored tracked physical data from the Activity data routine, and 3) any of the monitored personal communication, the monitored past and future event information, or the monitored fact-based information logged or scheduled in the one or more time synchronous applications. The insight engine is configured to generate notifications with suggestions regarding any of i) sleep activity and ii) physical activity to the user of the wearable electronic device based on the correlations.

The insight engine can also make correlations based on the monitored tracked data from the Sleep data routine and the Activity data routine with events logged or scheduled in the one or more time synchronous application. The insight engine can generate notifications with suggestions regarding the sleep and physical activity to the user of the wearable electronic device based on at least events logged or scheduled in the one or more time synchronous applications.

The Activity data routine can either directly or by cooperation with the insight engine, communicate notifications to the user of the wearable electronic device. The notifications can be communicated by cooperation with any of i) a speaker in the wearable electronic device to emit an audible notification, ii) a vibrator in the wearable electronic device to communicate a vibration notification, iii) a display screen to display information on the display screen to communicate a visual notification, and iv) any combination of these to the user of the wearable device. The insight engine can then generate the notifications with suggestions regarding the sleep and physical activity to the user.

In an embodiment, a method of executing a lifestyle service is discussed. The method of executing a lifestyle service includes health service functionality on a wearable electronic device and has a number of example steps. The data and routines associated with the lifestyle service can be stored in a memory of the wearable electronic device. The lifestyle service, includes at least i) a Sleep data routine and ii) an Activity data routine, that can be executed by a processor of the wearable electronic device. The lifestyle service can be configured to cooperate with an insight engine. Data can be collected and tracked on a physical activity of the user of the wearable electronic device by the Activity data routine. The Activity data routine can collect data via cooperation with any of an accelerometer, a magnetometer, a gyroscope, a barometer, a heart rate monitor and a light sensor, in the wearable electronic device. The tracked physical activity data can be stored in the memory of the wearable electronic device. The tracked physical activity data can be displayed on a display screen of the wearable electronic device. The average tracked physical activity data can be compared with the tracked physical activity data in set increments that occur at least once per hour. Notifications can be communicated, either directly or by cooperation with the insight engine, to the user of the wearable electronic device. Notifications can be communicated by cooperation with any of i) a speaker in the wearable electronic device to emit an audible notification, ii) a vibrator in the wearable electronic device to communicate a vibration notification, iii) a display screen to display information on the display screen to communicate a visual notification, and iv) any combination of these to the user of the wearable device.

The insight engine can monitor the time synchronous applications. The time synchronous applications include any application that is configured to keep a time synchronized organization of at least two of i) personal communication information, ii) past and future event information, and iii) fact-based information, each of which are logged or scheduled in the one or more time synchronous applications. The applications can include but are not limited to a timeline application and a calendar application. The applications can reside either on the wearable electronic device, a server or on a mobile computing device, such as a smart phone, that can cooperate and communicate with the wearable electronic device.

The insight engine can monitor the tracked data from the Sleep data routine and the Activity data routine. The monitored tracked data from the Sleep data routine and the Activity data routine as well as events logged or scheduled in the one or more time synchronous applications can be correlated by the insight engine. Notifications can be generated by the insight engine with suggestions regarding sleep and physical activity to the user of the wearable electronic device. The notification and suggestion can be based on at least the events, including information, logged or scheduled in the time synchronous applications. The insight engine can monitor the tracked data of the Sleep data routine, the tracked data of the Activity data routine, and any historical tracked data for any of these routines. The insight engine can then compare the data to the events logged or scheduled in the time synchronous applications in order to generate the notifications with suggestions regarding the sleep and physical activity to the user.

The insight engine can also make correlations based on at least two of 1) the monitored tracked sleep data from the Sleep data routine, 2) the monitored tracked physical data from the Activity data routine, and 3) any of the monitored personal communication, the monitored past and future event information, or the monitored fact-based information logged or scheduled in the one or more time synchronous applications. The insight engine is configured to generate notifications with suggestions regarding any of i) sleep activity and ii) physical activity to the user of the wearable electronic device based on the correlations.

BRIEF DESCRIPTION OF THE DRAWINGS

The multiple drawings refer to the example embodiments of the design.

Figure 1A:
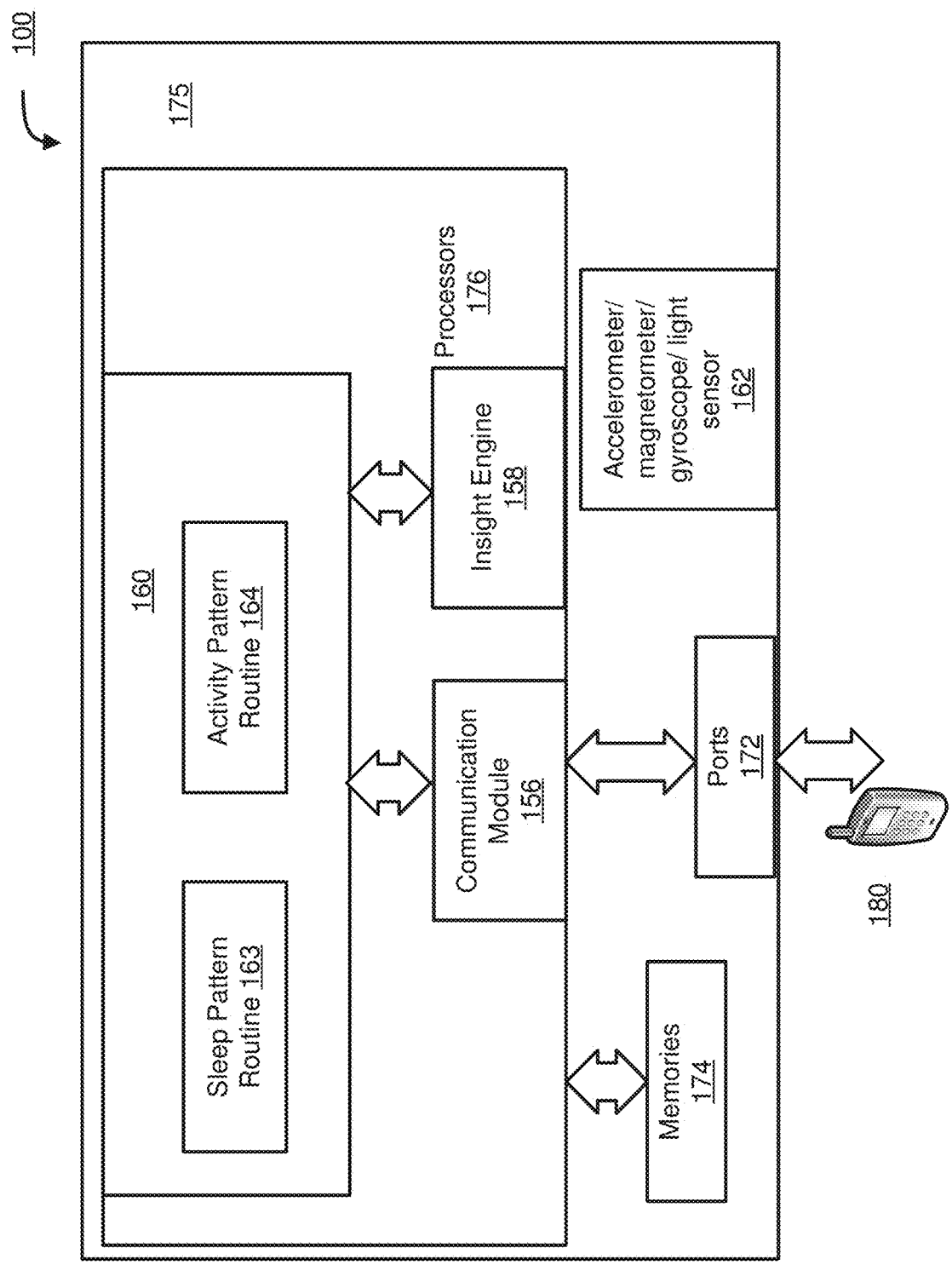
FIG. 1A illustrates a block diagram of an example wearable electronic device.

While the design is subject to various modifications and alternative forms, specific embodiments thereof have been shown by way of example in the drawings and will herein be described in detail. The design should be understood to not be limited to the particular forms disclosed, but on the contrary, the intention is to cover all modifications, equivalents, and alternatives falling within the spirit and scope of the design.

DETAILED DISCUSSION

In the following description, numerous specific details are set forth, such as examples of wearable electronic devices, named components, connections, number of databases, etc., in order to provide a thorough understanding of the present design. It will be apparent; however, to one skilled in the art that the present design may be practiced without these specific details. In other instances, well known components or methods have not been described in detail but rather in a block diagram in order to avoid unnecessarily obscuring the present design. Thus, the specific details set forth are merely exemplary. The specific details discussed in one embodiment may be reasonably implemented in another embodiment. The specific details may be varied from and still be contemplated to be within the spirit and scope of the present design.

In general, a lifestyle service that includes but is not limited to health service functionality with data and routines is discussed. The lifestyle service can include various routines including i) a Sleep data routine, ii) an Activity data routine, and iii) a State of Mind routine. The lifestyle service can also cooperate with an insight engine.

The Activity data routine can collect and track data on a physical activity of the user of the wearable electronic device. The Activity data routine can collect data by cooperation with sensors, which include any of an accelerometer, a magnetometer, a gyroscope, and a light sensor, in the wearable electronic device. The Activity data routine can then store the tracked physical activity data in the memory of the wearable electronic device. The Activity data routine can also cooperate with a graphic user interface to display the tracked physical activity data on a display screen of the wearable electronic device.

Likewise, the Sleep data routine can collect and track data on a sleep pattern of the user of the wearable electronic device. The Sleep data routine can cooperate with any of the accelerometer, the magnetometer, the gyroscope, and the light sensor, in the wearable electronic device to collect data. The Sleep data routine can store the tracked sleep data in the memory of the wearable electronic device. The Sleep data routine can cooperate with the graphic user interface to display the tracked sleep pattern data on the display screen of the wearable electronic device.

The insight engine can any of i) compare a current average tracked physical activity data or tracked sleep data to a historical average of the tracked data in a set increment of time, such as at least once per hour, and/or ii) compare a total amount of current tracked physical activity data to a historical total amount of tracked physical activity data in the set increment of time. The Activity data routine can either directly or by cooperation with the insight engine, communicate notifications to the user of the wearable electronic device. The notifications to the user of the wearable device can be sent by cooperation with any of i) a speaker in the wearable electronic device to emit an audible notification, ii) a vibrator in the wearable electronic device to communicate a vibration notification, iii) a display screen to display information on the display screen to communicate a visual notification, and iv) any combination of these.

The insight engine is configured to provide suggestions including guidance, coaching, suggested actions, feedback, etc. The insight engine can also generate notifications with suggestions regarding sleep activity, physical activity, and mood or state of mind for the user of the wearable electronic device. The lifestyle service is aware of information contained in one or more time synchronous applications. The lifestyle service and insight engine cooperate to compare tracked physical activity data with historical data in set increments in light of the information in the time synchronous applications and then communicate insightful notifications to the user.

FIG. 1A illustrates a block diagram of an example human wearable device. The block diagram 100 shows a human wearable device 175 that can communicate with a mobile device such as a smart phone 180. The human wearable device includes one or more processors 176, memories 174, and ports 172. The lifestyle service 160 that includes at least includes Activity data routine 164 and Sleep data routine 163 can execute on the processors 176. The human wearable device also includes a communication module 156 that can run on the processors and for communicating to outside of the human wearable devices.

As described, in an embodiment, a wearable electronic device 175 can include one or more processors 176. The processors can execute the lifestyle service 160 that at least includes Activity data routine 164 and Sleep data routine 163. The wearable electronic device 175 can include a communication module 156 such that the lifestyle service 160 can communicate through the communication module with a mobile device 180 through ports 172. In addition, the lifestyle service routines can be stored in the memories 174 of wearable electronic device 175. The communication module 156 can transmit wirelessly through a network to another computing device such as a mobile device 180 cooperating with the wearable electronic device. (See, for example, FIGS. 7-8). In an example, the wearable electronic device 175 and the mobile device 180 can directly communicate using Bluetooth. In other embodiments, the communication may occur thru Zigbee, Wi-Fi, cellular network, or other.

In an embodiment, the lifestyle service 160 with data and routines can be stored in executable format in a memory 174 in a wearable electronic device 175. A processor 176 in the wearable electronic device 175 can execute the routines of the lifestyle service. The lifestyle service can include at least two routines i) a Sleep data routine 163 and ii) an Activity data routine 164. Also, the lifestyle service can cooperate 160 with an insight engine 158. In an example, the insight engine 158 is in the mobile device 180. The insight engine 158 can i) execute on a web server and communicate through a mobile computing device, such as a smart phone, with the wearable electronic device, ii) execute on the mobile computing device and communicate with the wearable electronic device, iii) execute on the processors of the wearable electronic device, or iv) execute on any combination of the three implementations above.

In an embodiment, the insight engine 158 can monitor one or more time synchronous applications. The insight engine 158 can monitor, by pulling information from or receiving information from, one or more time synchronous applications. The time synchronous applications include any application that is configured to keep a time synchronized organization of at least two of i) personal communication information, ii) past and future event information, and iii) fact-based information, each of which are logged or scheduled in the one or more time synchronous applications. For example, time synchronous applications include but are not limited to a timeline application and a calendar application. The synchronous applications can reside either on the wearable electronic device or on a mobile computing device that can cooperate and communicate with the wearable electronic device. The timeline application can have such events or information logged in a time format such as personal communication information, past and future event information and fact-based information. Personal communication can include emails, tweets, text messages, facebook notifications, and more. Event information can include calendar events or reminders. Fact based information can include sport scores, weather information, etc.

Some example types of information scheduled or logged into the time synchronous applications can include at 4 AM a weather event of rain, at 5:10 AM sunrise, at 5:15 AM wake-up alarm, at 6:10 AM a missed telephone call, a calendar event for a lunch meeting from 11:30 to 1 PM, a business meeting from 3 PM to 4 PM, a workout at the gym from 7 to 8 PM. Each one of these time ordered information elements may come from the same or different sources, yet are arranged and placed in a useful time synchronized manner for the user.

The insight engine can also monitor tracked data from the Sleep data routine such as sleep pattern data and sleep activity data. The insight engine can then monitor the tracked data from the Sleep data routine, the tracked data from Activity data routine, any tracked data from a State of Mind routine, and any historical tracked data for any of these routines. The insight engine can make correlations based on the monitored tracked data from the Sleep data routine, the Activity data routine, and State of Mind routine, with events or information logged or scheduled in the one or more time synchronous application. The correlation may include evaluating and then making a nexus or conclusion from the evaluation. The insight engine is configured to make correlations based on at least two of 1) the monitored tracked sleep data from the Sleep data routine, 2) the monitored tracked physical data from the Activity data routine, and 3) any of the monitored personal communication, the monitored past and future event information, or the monitored fact-based information logged or scheduled in the one or more time synchronous applications. The insight engine can generate notifications with suggestions regarding any of i) sleep activity and ii) physical activity to the user of the wearable electronic device based on the correlations. The insight engine can also generate notifications with suggestions regarding the sleep and physical activity to the user of the wearable electronic device based on at least information events logged or scheduled in the one or more time synchronous applications. The insight engine can monitor the tracked data of the Sleep data routine, the tracked data of the Activity data routine, and any historical tracked data for any of these routines and then compare the data to the events logged or scheduled in the one or more time synchronous applications. The insight engine can then generate the notifications with suggestions regarding the sleep and physical activity to the user.

Figure 4:
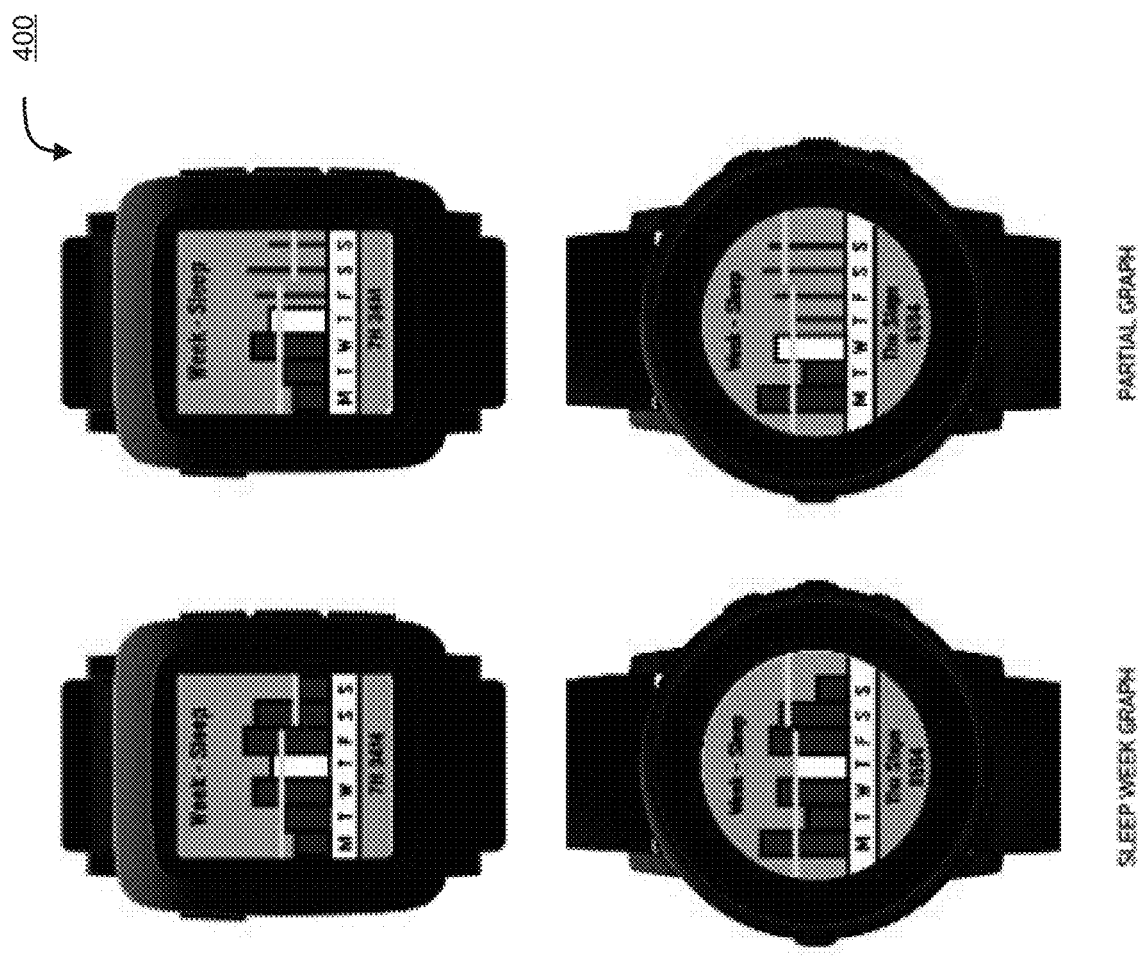
FIG. 4 illustrates wearable electronic devices showing examples of human sleep information.

Additionally, the insight engine 158 can 1) execute on a web server 204A and communicate through the mobile computing device 180 with the wearable electronic device, 2) execute on the mobile computing device 180 and communicate with the wearable electronic device, 3) execute on the processor of the wearable electronic device as shown in FIG. 1A, 4) execute on any combination of the three implementations above. In an example, the insight engine 158 is resident in the mobile device 180.

Additionally, a wearable electronic device can have one or more memories 174 and one or more processors 176. The wearable electronic device can also have one or more of 162:

an accelerometer, a magnetometer, a gyroscope, a barometer, a heart rate sensor, and a light sensor. The wearable electronic device can further include a graphic user interface and a display screen, one or more of a speaker and a vibrator, a communication module that can execute on the processors 176, an insight engine 158, and a lifestyle service 160. The wearable electronic device can have its own global positioning system chip and GPS app or merely have a routine configured to pull information from a GPS app on a cooperating mobile device.

Figure 1B:
FIG. 1B illustrates wearable electronic devices showing examples of human sleep information.
Figure 6:
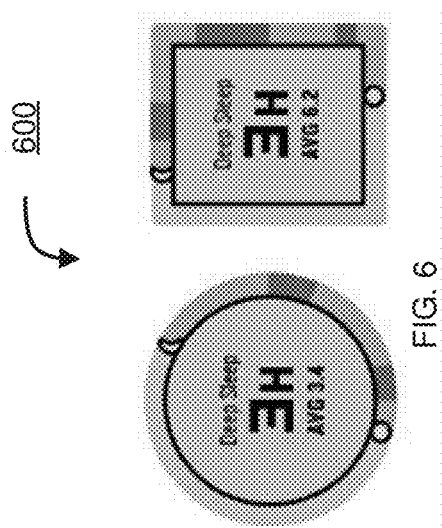
FIG. 6 illustrates wearable electronic devices showing examples of sleep information.

FIGS. 1B and 6 illustrates human wearable electronic devices showing examples of sleep information.

In an embodiment, the Sleep data routine can collect and track data on a sleep pattern of the user of the wearable electronic device 175. The Sleep data routine can collect data via cooperation with any of the accelerometer, the magnetometer, the gyroscope, and the light sensor, in the wearable electronic device, and can store the tracked sleep pattern data in the memory of the wearable electronic device. The Sleep data routine can cooperate with the graphic user interface to display the tracked sleep pattern data and/or tracked sleep activity data on the display screen of the wearable electronic device. For example, the user interface presents a bar around the displayed numerical data and the bar has lighter and darker shades to indicate a difference between deep sleep and regular sleep.

Figure 2:
FIG. 2 illustrates wearable electronic devices showing examples of human activity information.
Figure 3:
FIG. 3 illustrates wearable electronic devices showing examples of human activity information.
Figure 5:
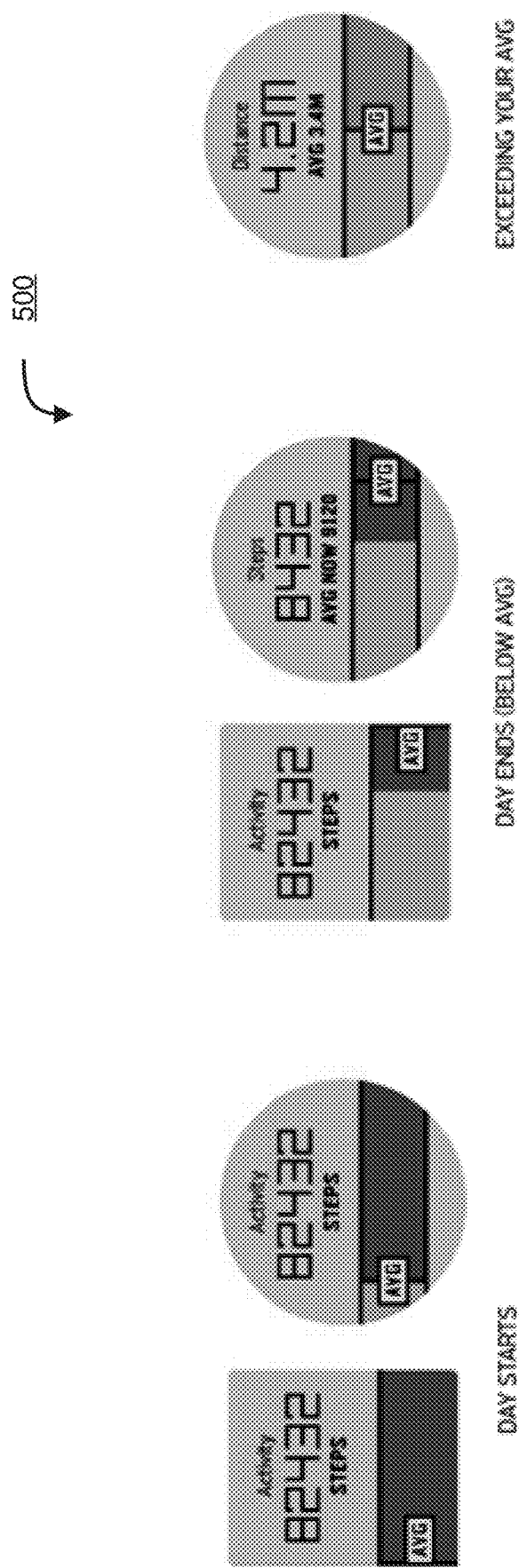
FIG. 5 illustrates wearable electronic devices showing examples of activity information.

FIGS. 2, 3 and 5 illustrates human wearable devices showing examples of activity information. For example, FIG. 3 illustrates the lifestyle service displaying the tracked physical activity data over a set period of time on the display. The set period of time can be shorter than a day such as an hour increment of time. In the example in FIG. 2, the tracked physical activity is shown vertically for each day of the week and the line going horizontally across shows the averages for the same increments of time for week days as a whole and week-end days as a whole. The lifestyle service may display the tracked physical activity data over a set period of time on the display so that the user can compare individual workouts and boost the user's performance on their next workout.

In an embodiment, the Activity data routine can collect and track data on a physical activity of a user of the wearable electronic device. The Activity data routine 164 can collect data via cooperation with any of an accelerometer, a magnetometer, a gyroscope, and a light sensor, in the wearable electronic device. The Activity data routine can store the tracked physical activity data in the memory 174 of the wearable electronic device. The Activity data routine can cooperate with a graphic user interface to display the tracked physical activity data on a display screen of the wearable electronic device. (See, for example, FIGS. 2, 3, 5, and 9.)

In an embodiment, the lifestyle service 160 can store tracked physical activity data and tracked sleep pattern data every minute. The lifestyle service 160 can then calculate average tracked physical activity data and average tracked sleep pattern data every 15 minutes. This can allow the lifestyle service to calculate averages at every minute of the day, further allowing the lifestyle service flexibility of both i) when during a day to trigger and provide the notification giving feedback on a relative goal of the day and ii) what a content of the suggestion should be based on either a current tracked physical activity data or current tracked sleep data compared to the relative goal of the day. Thus, how close the user is to achieving the goal is updated every 15 minutes.

In an embodiment, at least once per hour, an algorithm in the lifestyle service 160 is configured to track and then store one or more kinds of physical activities engaged in by the user, such as a number of steps taken. The algorithm can then also translate based on the user's height the number of steps taken into an amount of calories burned and distance traveled. The algorithm can also track the user's active time based on the type of changes detected in the user's movement as detected by the various sensors. The algorithm can also track other forms of user's exercise by configuring a number of scheduled physical activity periods and rest periods so that the user can compare individual workouts and boosts the user's performance on their next workout.

Thus, the lifestyle service can cooperate with the graphic user interface to display steps taken and calories burned by the user throughout a day. The lifestyle service can also display user's current step counts and progress towards user's daily goal. The user can get a vibration when the user reaches daily average. In other embodiments, the user may get a vibration on reaching individually set goals or for other achievements. The lifestyle service cooperating with the graphic user interface can display graphs of individual workouts on daily, weekly, or monthly basis and to display tracked physical activity including daily progress and summary data for a user selectable amount of days.

Figure 9:
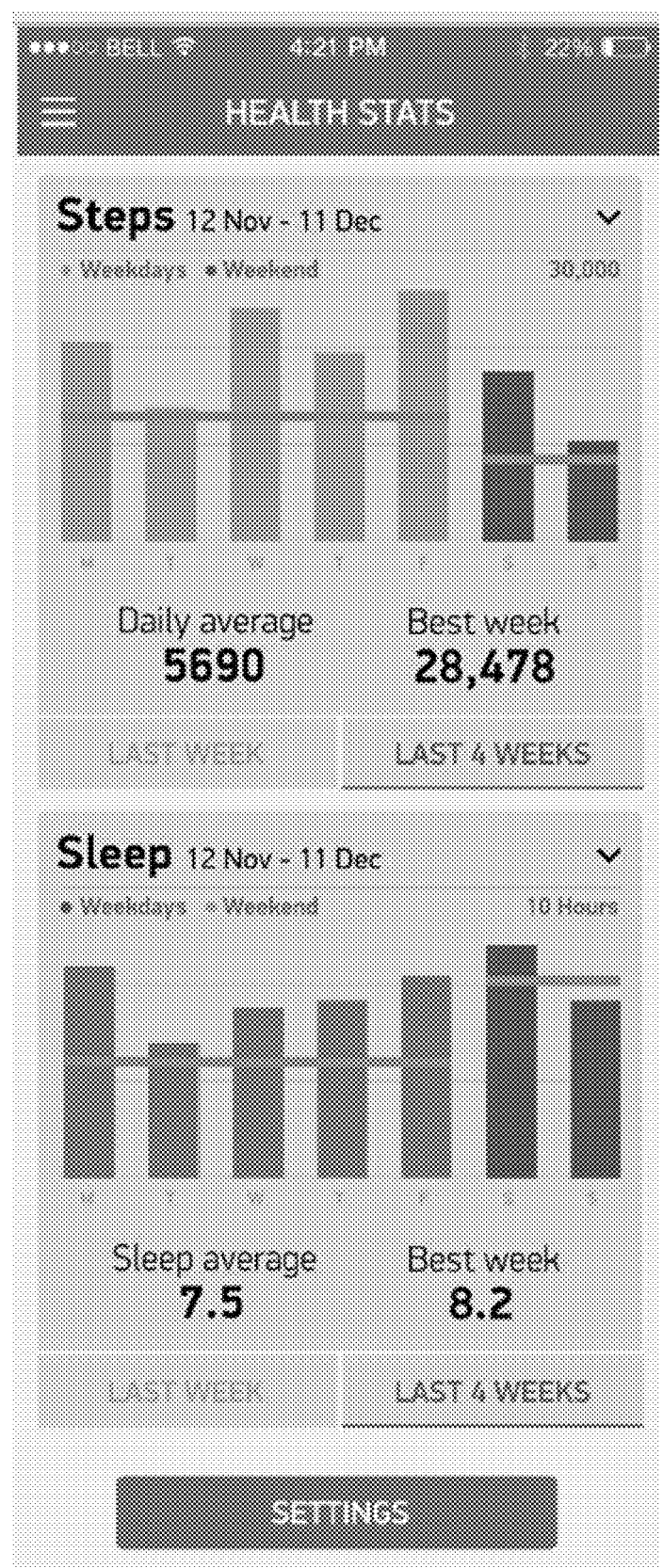
FIG. 9 illustrates wearable electronic devices showing examples of sleep and activity information.

FIGS. 4 and 9 illustrate human wearable devices showing examples of both physical activity and sleep information.

FIG. 4 illustrates human wearable electronic devices showing examples of sleep information display as current activity in vertical bar graphs and averages for weekdays and weekend days indicated by a horizontal line across the graph. The Sleep data routine is configured to collect and track data on the sleep data of the user of the wearable electronic device, via cooperation with sensors 887, which include any of the accelerometer, the magnetometer, the gyroscope, the barometer, the heart rate sensor, and the light sensor, in the wearable electronic device. The Sleep data routine may store the tracked sleep data in the memory of the wearable electronic device. The Sleep data routine may cooperate with the graphic user interface to display the tracked sleep data on the display screen of the wearable electronic device. The Sleep data routine and/or the insight engine may be configured to any of i) track a current average tracked sleep data in a set increment of time and ii) compare a current total amount of sleep data in the set increment of time to any historical tracked data for the same increment of time. The set increment of time may be, for example, less than a twenty-four hour period of time, which is shown on the display screen. The Sleep data routine is configured to either directly or by cooperation with the insight engine, communicate the notifications regarding sleep to the user of the wearable electronic device by cooperation with any of i) the speaker in the wearable electronic device to emit an audible notification, ii) the vibrator in the wearable electronic device to communicate a vibration notification, iii) the display screen to display information on the display screen to communicate a visual notification, and iv) any combination of these to the user of the wearable device.

Next, in an example, the lifestyle service can both log and track specific activities such as sleep data that occur in the fixed increments of less than an hour. The lifestyle service then may compare the current logged activity to previous tracked activity for the same period of tracked time. For example, in FIG. 6 the lifestyle service cooperates with the display to show the user had 3.0 hours of deep sleep last night while the user's historical average is 3.4 hours of deep sleep for that same increment of time. Both the Sleep data routine and the Activity data routine can track the data in set increments that occur at least once per hour, such as every minute of the day. Both the Sleep data routine and the Activity data routine then store this data in the memory of the wearable electronic device. The locally stored data in the memory of the wearable electronic device may be then periodically sent to a server and database of the insight engine to store this data as historical data on the user.

In an embodiment, the insight engine 160 can monitor all four of the Sleep data routine, the Activity data routine, the State of Mind routine, and any set goals for any of these routines. The insight engine is then configured to take an action of adding an event corresponding to any of a sleep activity of the user, the physical activity of the user, or a mood of the user back into any of the time synchronous applications when the set goals for the sleep activity, the physical activity, or the mood of the user are not yet met.

Figure 10:
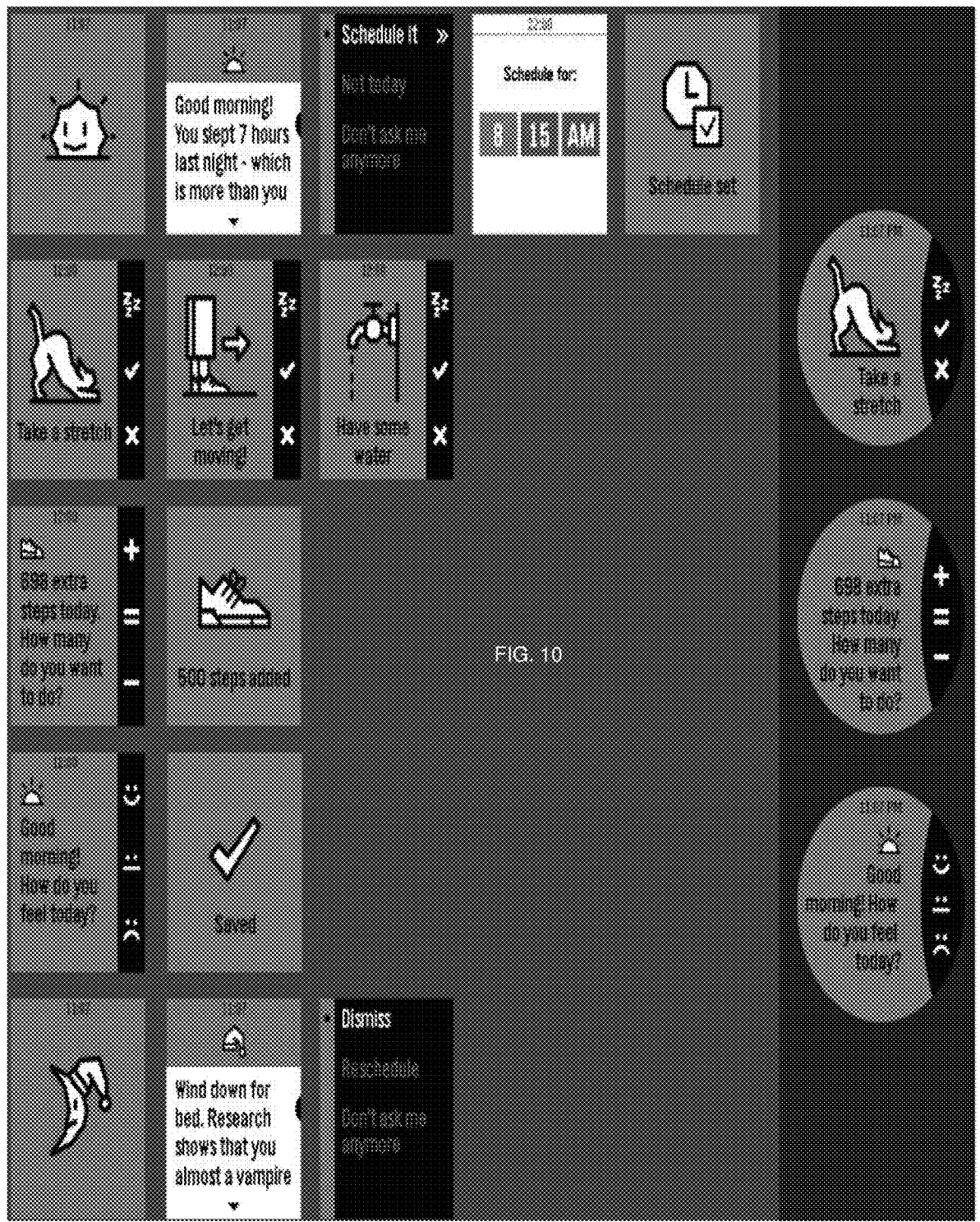
FIG. 10 illustrates wearable electronic devices showing notifications displayed for the wearer.

FIG. 10 illustrates human wearable devices showing notifications displayed for the human wearer. For example, but not limited to a notification may convey to the user that they need to take 500 steps. A notification may communicate to the user that they, for example, slept 7 hours, which is more than the user's historical average for a night. A notification may convey to the user that they, for example, should take a stretch to achieve their physical activity goal for that hour. A notification may communicate to the user many other insightful suggestions based on the insight engine making correlations. A user may simply read a notification or may take an action, such as the "zzz" option, embedded in the notifications, which makes the notification pop up again at a later point in time.

The insight engine can monitor tracked sleep data from the Sleep data routine and tracked physical activity data from the Activity data routine. The insight engine can make correlations based on at least two of 1) the monitored tracked sleep data, including current and historical tracked data, from the Sleep data routine, 2) the monitored tracked physical data, including current and historical tracked data, from the Activity data routine, and 3) any of the monitored personal communication, the monitored past and future event information, or the monitored fact-based information logged or scheduled in the one or more time synchronous applications. The insight engine is configured to generate notifications with suggestions regarding any of i) sleep activity and ii) physical activity to the user of the wearable electronic device based on these correlations.

The lifestyle service may be configured to generate some of the notifications with suggestions regarding sleep and the physical activity based on a previous day's individual effort. In an embodiment, the insight engine can compare a current tracked physical activity data to historical averages of the tracked data and then cross reference any events or information scheduled in the time synchronous applications in order to decide both 1) whether to generate the notification at this time and then 2) what to convey in the notification. The insight engine has one or more routines configured to both 1) decide whether to send the notification with the suggestion and 2) what to convey in the notification based on a comparison of factors of i) remaining physical activity still needed to achieve a historical average amount of physical activity, ii) what types of events are yet to still occur according to events currently scheduled in the one or more time synchronous applications, and iii) a time duration associated with each of the currently scheduled events yet to occur in that day. Thus, the insight engine can use historical averages of tracked data to control a trigger of when to send a notification with suggestions regarding sleep, activity, and mood that may require actions by a user.

As an example, if the user has not slept very well, the insight engine can suggest the user to go to bed earlier and/or set a pin on the timeline application. In another example, if user's steps are under average, the insight engine can look at user's timeline application and suggest a time for taking a walk. If the user's goal is to sleep a certain amount of hours and the insight engine sees that the user has an event such as an 8 AM meeting, and then the insight engine can send a notification suggesting the user to go to bed early.

In an embodiment, the insight engine can compare the current tracked data to historical averages of the tracked data and then correlated this with the events logged/scheduled in the time synchronous applications in order to decide both whether to generate a notification at this time and then what to convey in the notification.

Thus, the insight engine can evaluate what type of event is logged in the time synchronous applications in order to decide whether to generate a notification at this time by comparing properties of the event that may include duration, timing, category and location.

The insight engine may evaluate tracked data from typically unassociated data sources of i) sleep activity from the Sleep data routine, ii) physical activity from the Activity data routine, and iii) scheduled events on any of the time synchronous applications in order to make beneficial notifications with suggestions regarding the sleep activity and the physical activity to the user of the wearable electronic device. The insight engine may evaluate what type of event is scheduled in the time synchronous application by comparing properties of the event that may include, but are not limited to, duration, timing, category and location. The insight engine is configured to decide whether to generate the notification at this time by comparing the types of scheduled events that have not yet occurred to an amount of either sleep activity or physical activity the user still needs to achieve a set goal. Thus, the insight engine may provide an insightful suggestion in the notification on achieving that set goal rather than an arbitrary posting of the set goal.

The lifestyle service is configured to i) collect tracked data from the Sleep data routine, the Activity data routine, and the State of Mind routine, ii) push notifications with suggestions from the insight engine, and iii) display current tracked data as well as historical tracked data.

In another embodiment, lifestyle service is configured to i) collect tracked data from the Sleep data routine, the Activity data routine, and the State of Mind routine, ii) correlate the collected information with the event based information, fact based information or personal communication information to generate notifications ii) push notifications with suggestions from the insight engine, and iii) display current tracked data as well as historical tracked data.

The Activity data routine can either directly or by cooperation with the insight engine 158, communicate notifications to the user of the wearable electronic device by cooperation with any of i) a speaker 897 in the wearable electronic device to emit an audible notification, ii) a vibrator 899 in the wearable electronic device to communicate a vibration notification, iii) a display screen 891 to display information on the display screen to communicate a visual notification, and iv) any combination of these to the user of the wearable device. In an embodiment, a separate routine (not the activity data routine nor the insight engine) is configured to work with both of these two to determine and communicate the notifications.

Likewise, the Sleep data routine can compare average tracked sleep pattern data with the tracked sleep pattern data in set increments that occur at least once per day. The Sleep data routine can either directly or by cooperation with the insight engine, communicate notifications to the user of the wearable electronic device. The Sleep data routine can send the notifications through any of i) the speaker in the wearable electronic device to emit an audible notification, ii) the vibrator in the wearable electronic device to communicate a vibration notification, iii) the display screen to display information on the display screen to communicate a visual notification, and iv) any combination of these to the user of the wearable device. In an embodiment, a separate routine (not the sleep data routine nor the insight engine) is configured to work with both of these two to determine and communicate the notifications.

Figure 11:
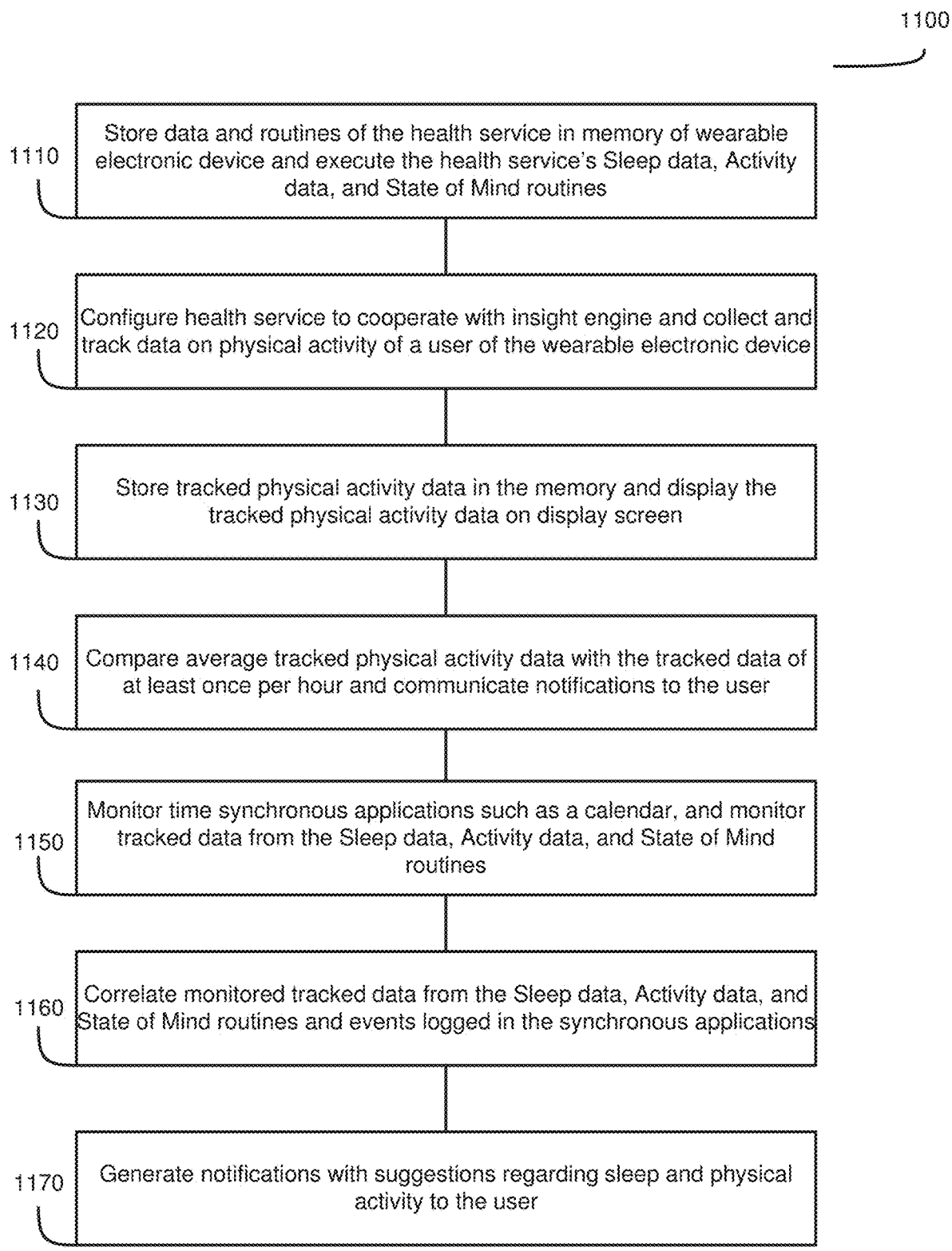
FIG. 11 illustrates a flow graph of an example method to execute a lifestyle service on a wearable electronic device.

FIG. 11 illustrates a flow graph of an example method to execute a lifestyle service on a wearable electronic device. The flow diagram 1100 can be used for describing the method and the steps may be performed out of literal order when logically possible. Data and routines of the lifestyle service are stored in the memory of wearable electronic device. The health service's Sleep data routine, State of Mind routine, and Activity data routines can be executed (1110) by one or more processors. As an example, the flow diagram 1100 can be executed on the human wearable device 100 of FIG. 1A.

The lifestyle service is configured to cooperate with insight engine to collect and track data on physical activity of a user of the wearable electronic device (1120). Data collection can be done via cooperation with any of an accelerometer, a magnetometer, a gyroscope, barometer, heart rate monitor and a light sensor, in the wearable electronic device. (See, for example, FIG. 1A.)

The tracked physical activity data is stored in the memory and the tracked physical activity data displayed on a display screen (1130). As an example, FIGS. 2, 3, 5, and 9 display physical activity data.

Average tracked physical activity data is compared with the tracked data for at least once per hour and notifications are communicated to the user (1140). The notification related to physical activity data can be sent directly by the lifestyle service 160 or can be send by the lifestyle service cooperating with the insight engine 158. In an example, the insight engine can do data analysis and comparison for the lifestyle service and the lifestyle service can send the notification.

Time synchronous applications such as a calendar are monitored, as well as the tracked data from the State of Mind routine, the Sleep data routine, and the Activity data routine are monitored (1150). The time synchronous applications include any application that is configured to keep a time synchronized organization of at least two of i) personal communication information, ii) past and future event information, and iii) fact-based information, each of which are logged or scheduled in the one or more time synchronous applications (1150). In an example, these time synchronous applications include but are not limited to a timeline or a calendar, which are monitored by the insight engine. The time synchronous applications can reside on the human wearable device or on a mobile device coupled to the human wearable device. Likewise, the insight engine can reside on the human wearable device or the mobile device. In another example, the insight engine and the time synchronous applications can reside on a webserver and the monitoring can be performed by the webserver. Then the webserver can communicate through the mobile device to the human wearable device. In yet another example, the insight engine and the time synchronous applications can be distributed between the human wearable device, the mobile device, and the webserver. The webserver and the mobile device can wirelessly communicate and the human wearable device and the webserver can wirelessly communicate via the mobile device. The insight engine may monitor these one or more time synchronous applications by pulling information from or receiving information from the one or more time synchronous applications (1150).

The monitored tracked data from Sleep data routine, State of Mind routine, and Activity data routine are correlated with the events logged in the synchronous applications (1160). The insight engine can correlate the tracked data and the events. As an example, an event can be a scheduled meeting or an appointment.

Additionally, the insight engine may correlate based on at least two of 1) the monitored tracked sleep data from the Sleep data routine, 2) the monitored tracked physical data from the Activity data routine, and 3) any of the monitored personal communication, the monitored past and future event information, or the monitored fact-based information logged or scheduled in the one or more time synchronous applications (1160). The insight engine may generate notifications (1170) with suggestions regarding any of i) sleep activity and ii) physical activity to the user of the wearable electronic device based on the correlations (1160).

Notifications with suggestions regarding sleep and physical activity to the user are generated (1170). The notifications can be generated by the insight engine. The notifications can suggest actionable items. As an example, after analyzing the tracked data, the insight engine can realize the user's physical activity is below daily average and there is no scheduled meeting or appointment on the user's calendar in the next few hours. Then, the insight engine may send a notification suggesting the user to take a walk. In another example, the insight engine may acquire weather reports from the webserver and suggest taking a walk only if weather conditions permit.

Figure 7:
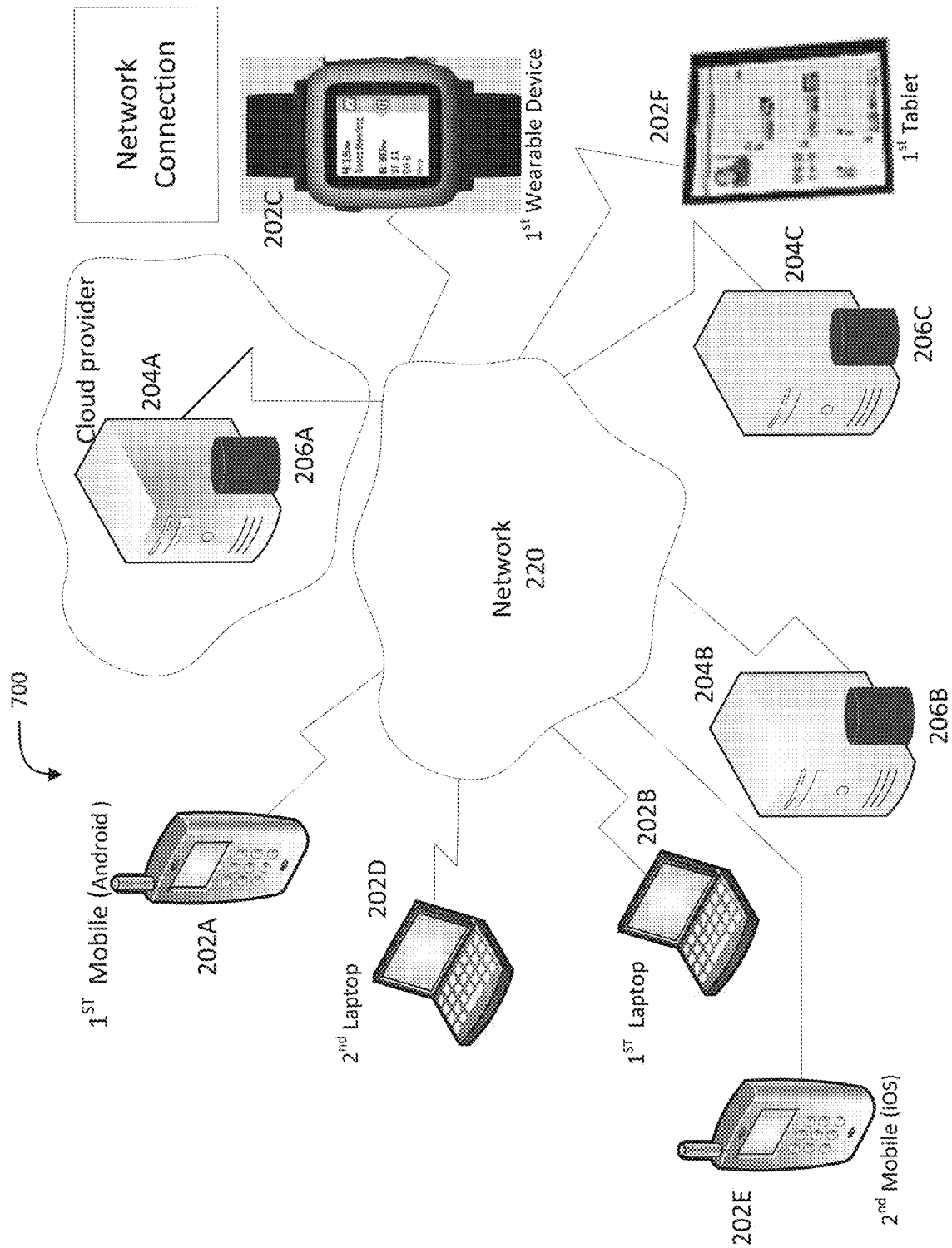
FIG. 7 illustrates a block diagram of an embodiment of remote access and/or communication by a wearable electronic device to other devices on a network.
Figure 8:
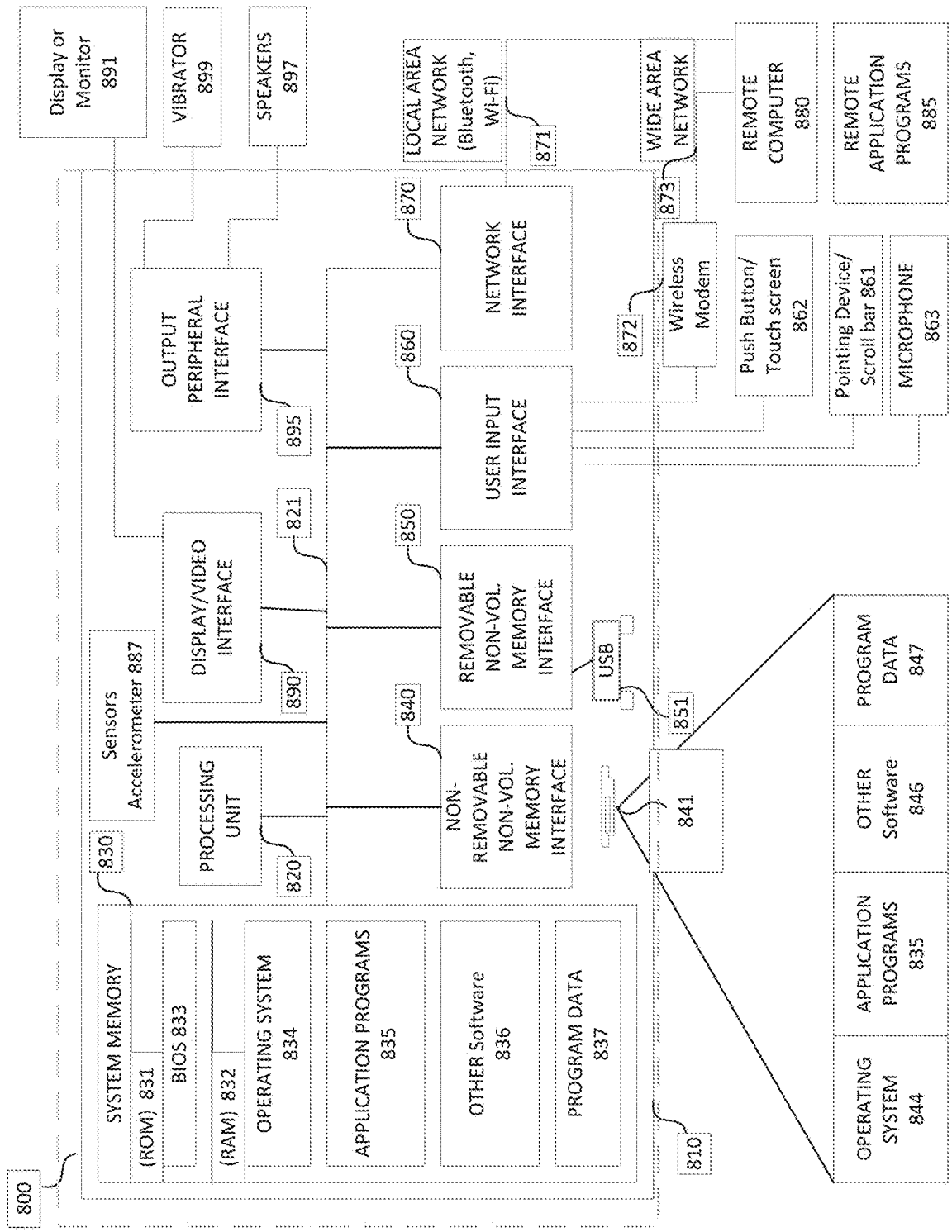
FIG. 8 illustrates a block diagram of an example computing system that may be part of an embodiment of one or more of the wearable electronic devices discussed herein.

Next, in general, the wearable electronic device includes one or more systems and can be coupled to one or more networks. FIGS. 7-8 illustrates additional example environments to implement the concepts.

In an embodiment, the wearable electronic device is a smart watch which features a black and white Sharp Memory LCD display screen, a programmable CPU, memory, storage, Bluetooth, a vibrating motor, a magnetometer, an ambient light sensor, and an accelerometer. These features extend the smart watch's use beyond just displaying the time on the display screen and into many roles including interacting with smartphone notifications, activity tracking, gaming, map display, golf tracking, and more. The smart watch is compatible with Android and iOS devices. When connected to one of these devices via Bluetooth, the smart watch can (but may not need to) pair with that device and vibrate and display text messages, fitness information, emails, incoming calls, and notifications from social media accounts. The smart watch can also act as a remote control for the phone function in the paired device, or for other paired devices containing a camera such as the GoPro. As an example, an associated app store can provide a software development kit (SDK) to develop applications and watchfaces associated with the smart watch.

In another embodiment, the wearable electronic device may be a belt, a necklace, lapel pin or other form of wearable device.

The housing also has a computer readable storage medium in the housing accessible to the processor for storing instructions executable by the processor to generate the number of different operations on the onscreen display.

FIG. 8 illustrates a block diagram of an example computing system that may be used in an embodiment of one or more of the servers, a wearable electronic device, and client devices discussed herein. The computing system environment 800 is only one example of a suitable computing environment, such as a client device, server, wearable electronic device, etc., and is not intended to suggest any limitation as to the scope of use or functionality of the design of the computing system 810. Neither should the computing environment 800 be interpreted as having any dependency or requirement relating to any one or combination of components illustrated in the exemplary operating environment 800.

In an embodiment, the wearable electronic device is an electronic smartwatch that comes with a Gorilla Glass 64-color LED e-paper display, with 144×168 pixels and a pixel density of 182 ppi. The wearable electronic device has a color display, and still retains a backlight as well. The wearable electronic device also has a vibrating motor for silent alarms, and smart notifications. The wearable electronic device can have a redesigned charging cable that can magnetically attach itself to the wearable electronic device in order to maintain its water resistance. The wearable electronic device can also be equipped with an ambient light sensor, 6 axis accelerometer, etc. In an example, the wearable electronic device can have axis accelerometer with gesture detection, a vibrating motor, an ambient light sensor, a compass, a gyro meter, a magnetometer, a pedometer, a microphone, and four physical buttons for user input. In alternative embodiments, the display may include a touch screen, a scroll bar, one or more buttons, a rotating bezel or a combination of any of the elements for user input.

In an example, the display can have 144×168 pixel Sharp Memory LCD "e-paper", or 144×168 pixel black and white memory LCD using an ultra low-power "transflective LCD" with a backlight, or 1.25 inch 64-color LED backlit e-paper display.

In an embodiment, the wearable electronic device can connect through a wireless network to an app store having many applications and watchfaces that can be downloaded. The applications include notifications for emails, calls, text messages & social media activity; stock prices; activity tracking (movement, sleep, estimates of calories burned); remote controls for smartphones, cameras & home appliances; turn-by-turn directions (using the GPS receiver in a smartphone or tablet); display of RSS or JSON feeds; and also include hundreds of custom watch faces.

In an embodiment, the wearable electronic device can originally be shipped with applications pre-installed. These applications can use data received from a connected phone for distance, speed, and range information. The applications can also directly connect to a backend server on the cloud. More applications are downloadable via a mobile phone or tablet, and an SDK is freely available.

In an embodiment, the wearable electronic device can integrates with any phone or tablet application that sends out native iOS or Android notifications.

In an embodiment, the wearable electronic device's firmware operating system is based on a Free RTOS kernel and uses Newlib, the STM32 Peripheral Lib, the Ragel state machine compiler, and a UTF-8 Decoder. As an example, the wearable electronic device includes a 64-color e-paper display with Gorilla Glass, a thinner and more ergonomic chassis, plastic casing and a microphone. In an example, the wearable electronic device can have a Marine Grade steel chassis encasing with bezel and a PVD matte polishing finish and a tough 2.5D color e-paper display.

In an embodiment, the wearable electronic device is an electronic watch and includes a small accessory port on the back of the watch face. Open hardware platform of the wearable electronic device lets developers develop new third-party straps that connects to a special port at the back of the watch and can add additional features like GPS, heart rate monitors, extended battery life and other things to the watch. It enables the wearer to attach additional equipment to the watch, including sensors, batteries, etc.

In an embodiment, the Activity data routine 164 can collect and track data from two or more different types of physical activities of the user of the wearable electronic device 100. The Sleep data routine 163 can also collect, store, and track the sleep data which consists of one or more patterns of sleep of the user, such as stages of sleep including deep or regular sleep, as well as one or more sleep activities, such as total amount of sleep, of the user of the wearable electronic device.

In an embodiment, the lifestyle service can further include a State of Mind routine. The State of Mind routine can be activated by the user, and if activated, the user interface is configured to periodically ask the user questions about a user's mood. The user can be offered a choice of responding to the mood questions by either inputting a reply or by declining to respond. The State of Mind routine can store the mood pattern responses in the memory 174 of the wearable electronic device. The insight engine is configured to both monitor these mood responses and make correlations based on these mood responses to generate notifications with suggestions on a mood of the user. The State of Mind routine can glean the user's state of mind from information in the time synchronous applications as well as things the routine gleans from how the user reacts to any suggestions given by the lifestyle service as well as the user's response to the mood questions.

Thus, the lifestyle service also includes a State of Mind routine and the insight engine can monitor collected tracked data from the State of Mind routine and correlate the Mood data with the tracked physical activity data and tracked sleep pattern data. Then the lifestyle service can cross reference this data from the different sources of logged events in the time synchronous applications in order to generate a notification with suggestions regarding sleep, physical activity, and mood to the user.

Thus, the lifestyle service can be useful for both if the user intends to count steps for individual walking or other workouts, as well as if the user want to track all-day steps or cumulative physical activity workouts for the day.

In an embodiment, a web server can host the insight engine with logic for detecting a specific pattern of behavior for each user over a historical period of time greater than 2 days, as well as the webserver can have a list of notifications with suggestions preset in a library that can be accessed and additionally populated with the specific data for that user.

Computing System

With reference to FIG. 8, components of the computing system 810 may include, but are not limited to, a processing unit 820 having one or more processing cores, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) locale bus, and Peripheral Component Interconnect (PCI) bus.

Computing system 810 typically includes a variety of computing machine-readable media. Computing machine-readable media can be any available media that can be accessed by computing system 810 and includes both volatile and nonvolatile media, removable and non-removable media. By way of example, and not limitation, computing machine-readable mediums uses include storage of information, such as computer readable instructions, data structures, other executable software or other data. Computer storage mediums include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible medium which can be used to store the desired information and which can be accessed by computing device 800. Transitory media such as wireless channels are not included in the machine-readable media. Communication media typically embodies computer readable instructions, data structures, other executable software, or other transport mechanism and includes any information delivery media. As an example, some clients on network 220 of FIG. 7 may not have any optical or magnetic storage.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computing system 810, such as during start-up, is typically stored in ROM 831. RAM 832 typically contains data and/or software that are immediately accessible to and/or presently being operated on by processing unit 820. By way of example, and not limitation, FIG. 8 illustrates that RAM can include a portion of the operating system 834, other executable software 836, and program data 837.

The computing system 810 may also include other removable/non-removable volatile/nonvolatile computer storage media. By way of example only, FIG. 8 illustrates a solid-state memory 841. Other removable/non-removable, volatile/nonvolatile computer storage media that can be used in the exemplary operating environment include, but are not limited to, USB drives and devices, flash memory cards, solid state RAM, solid state ROM, and the like. The solid-state memory 841 is typically connected to the system bus 821 through a non-removable memory interface such as interface 840, and USB drive 851 is typically connected to the system bus 821 by a removable memory interface, such as interface 850.

As an example, the computer readable storage medium 841 stores Operating System software for smart watches to cooperate with both Android OS and iOS.

The drives and their associated computer storage media discussed above and illustrated in FIG. 8, provide storage of computer readable instructions, data structures, other executable software and other data for the computing system 810. In FIG. 8, for example, the solid state memory 841 is illustrated for storing operating system 844, other executable software 846, and program data 847. Note that these components can either be the same as or different from operating system 834, other executable software 836, and program data 837. Operating system 844, other executable software 846, and program data 847 are given different numbers here to illustrate that, at a minimum, they are different copies. In an example, the operating system, Pebble OS, can be a customized Free RTOS kernel that can communicate with Android and iOS apps using Bluetooth, Wi-Fi, cellular or other communication methodology.

A user may enter commands and information into the computing system 810 through input devices such as a keyboard, touchscreen, or even push button input component 862, a microphone 863, a pointing device and/or scrolling input component 861, such as a mouse, trackball or touch pad. The microphone 863 may cooperate with speech recognition software. These and other input devices are often connected to the processing unit 820 through a user input interface 860 that is coupled to the system bus, but may be connected by other interface and bus structures, such as a parallel port, game port or a universal serial bus (USB). A display monitor 891 or other type of display screen device is also connected to the system bus 821 via an interface, such as a display and video interface 890. In addition to the monitor, computing devices may also include other peripheral output devices such as speakers 897, a vibrator 899, and other output device, which may be connected through an output peripheral interface 890.

The computing system 810 may operate in a networked environment using logical connections to one or more remote computers/client devices, such as a remote computing device 880. The remote computing device 880 may be a wearable electronic device, a personal computer, a handheld device, a server, a router, a network PC, a peer device or other common network node, and typically includes many or all of the elements described above relative to the computing system 810. The logical connections depicted in FIG. 8 include a local area network (LAN) 871 and a wide area network (WAN) 873, but may also include other networks. Such networking environments are commonplace in offices, enterprise-wide computer networks, intranets and the Internet. A browser application may be resident on the computing device and stored in the memory.

When used in a LAN networking environment, the computing system 810 is connected to the LAN 871 through a network interface or adapter 870, which can be a Bluetooth or Wi-Fi adapter. When used in a WAN networking environment, the computing system 810 typically includes a modem 872, e.g., a wireless network, or other means for establishing communications over the WAN 873, such as the Internet. The wireless modem 872, which may be internal or external, may be connected to the system bus 821 via the user-input interface 860, or other appropriate mechanism. In a networked environment, other software depicted relative to the computing system 810, or portions thereof, may be stored in the remote memory storage device. By way of example, and not limitation, FIG. 8 illustrates remote application programs 885 as residing on remote computing device 880. It will be appreciated that the network connections shown are exemplary and other means of establishing a communications link between the computing devices may be used.

As discussed, the computing system may include a processor, a memory, a built in battery to power the computing device, an AC power input to charge the battery, a display screen, a built-in Wi-Fi circuitry to wirelessly communicate with a remote computing device connected to network.

It should be noted that the present design can be carried out on a computing system such as that described with respect to FIG. 8. However, the present design can be carried out on a server, a computing device devoted to message handling, or on a distributed system in which different portions of the present design are carried out on different parts of the distributed computing system.

Another device that may be coupled to bus 811 is a power supply such as a battery and Alternating Current adapter circuit. As discussed above, the DC power supply may be a battery, a fuel cell, or similar DC power source that needs to be recharged on a periodic basis. The wireless communication module 872 may employ a Wireless Application Protocol to establish a wireless communication channel. The wireless communication module 872 may implement a wireless networking standard such as Institute of Electrical and Electronics Engineers (IEEE) 802.11 standard, IEEE std. 802.11-1999, published by IEEE in 1999.

Examples of mobile computing devices may be a wearable electronic device, a laptop computer, a cell phone, a personal digital assistant, or other similar device with on board processing power and wireless communications ability that is powered by a Direct Current (DC) power source that supplies DC voltage to the mobile device and that is solely within the mobile computing device and needs to be recharged on a periodic basis, such as a fuel cell or a battery.

Network Environment

FIG. 7 illustrate diagrams of a network environment in which the techniques described may be applied. The network environment 700 has a communications network 220 that connects server computing systems 204A through 204C, and at least one or more client computing systems 202A to 202F. As shown, there may be many server computing systems 204A through 204C and many client computing systems 202A to 202F connected to each other via the network 220, which may be, for example, the Internet. Note, that alternatively the network 220 might be or include one or more of: an optical network, a cellular network, the Internet, a Local Area Network (LAN), Wide Area Network (WAN), satellite link, fiber network, cable network, or a combination of these and/or others. It is to be further appreciated that the use of the terms client computing system and server computing system is for clarity in specifying who generally initiates a communication (the client computing system) and who responds (the server computing system). No hierarchy is implied unless explicitly stated. Both functions may be in a single communicating device, in which case the client-server and server-client relationship may be viewed as peer-to-peer. Thus, if two systems such as the client computing system 202A and the server computing system 204A can both initiate and respond to communications, their communication may be viewed as peer-to-peer. Likewise, communications between the server computing systems 204A and 204-B, and the client computing systems 202A and 202C may be viewed as peer-to-peer if each such communicating device is capable of initiation and response to communication. Additionally, server computing systems 204A-204C also have circuitry and software to communication with each other across the network 220. One or more of the server computing systems 204A to 204C may be associated with a database such as, for example, the databases 206A to 206C. Each server may have one or more instances of a virtual server running on that physical server and multiple virtual instances may be implemented by the design. A firewall may be established between a client computing system 202C and the network 220 to protect data integrity on the client computing system 202C. Each server computing system 204A-204C may have one or more firewalls.

A cloud provider service can install and operate application software in the cloud and users can access the software service from the client devices. Cloud users who have a site in the cloud may not solely manage the cloud infrastructure and platform where the application runs. Thus, the servers and databases may be shared hardware where the user is given a certain amount of dedicate use of these resources. The user's cloud-based site is given a virtual amount of dedicated space and bandwidth in the cloud. Cloud applications can be different from other applications in their scalability which can be achieved by cloning tasks onto multiple virtual machines at run-time to meet changing work demand. Load balancers distribute the work over the set of virtual machines. This process is transparent to the cloud user, who sees only a single access point.

The cloud-based remote access is coded to utilize a protocol, such as Hypertext Transfer Protocol (HTTP), to engage in a request and response cycle with both a mobile device application resident on a client device as well as a web-browser application resident on the client device. The cloud-based remote access for a wearable electronic device, can be accessed by a mobile device, a desktop, a tablet device, and other similar devices, anytime, anywhere. Thus, the cloud-based remote access to a wearable electronic device hosted on a cloud-based provider site is coded to engage in 1) the request and response cycle from all web browser based applications, 2) SMS/twitter based request and response message exchanges, 3) the request and response cycle from a dedicated on-line server, 4) the request and response cycle directly between a native mobile application resident on a client device and the cloud-based remote access to a wearable electronic device, and 5) combinations of these.

In an embodiment, the server computing system 204A may include a server engine, a web page management component, a content management component, and a database management component. The server engine performs basic processing and operating system level tasks. The web page management component handles creation and display or routing of web pages or screens associated with receiving and providing digital content and digital advertisements. Users may access the server-computing device by means of a URL associated therewith. The content management component handles most of the functions in the embodiments described herein. The database management component includes storage and retrieval tasks with respect to the database, queries to the database, and storage of data.

An embodiment of a server computing system to display information, such as a web page, etc. is discussed. An application including any program modules, apps, services, processes, and other similar software executable when executed on the server computing system 204A, causes the server computing system 204A to display windows and user interface screens on a portion of a media space, such as a web page. A user via a browser from the client computing system 202A may interact with the web page, and then supply input to the query/fields and/or service presented by a user interface of the application. The web page may be served by a web server computing system 204A on any Hypertext Markup Language (HTML) or Wireless Access Protocol (WAP) enabled client computing system 202A or any equivalent thereof. For example, the client mobile computing system 202A may be a wearable electronic device, smart phone, a touch pad, a laptop, a netbook, etc. The client computing system 202A may host a browser to interact with the server computing system 204A. Each application has a code scripted to perform the functions that the software component is coded to carry out such as presenting fields and icons to take details of desired information. Algorithms, routines, and engines within the server computing system 204A take the information from the presenting fields and icons and put that information into an appropriate storage medium such as a database. A comparison wizard is scripted to refer to a database and make use of such data. The applications may be hosted on the server computing system 204A and served to the browser of the client computing system 202A. The applications then serve pages that allow entry of details and further pages that allow entry of more details.

Scripted Code

Any application and other scripted code components may be stored on a non-transitory computing machine-readable medium which, when executed on the machine causes the machine to perform those functions. The applications including program modules may be implemented as logical sequences of software code, hardware logic circuits, and any combination of the two, and portions of the application scripted in software code are stored in a non-transitory computing device readable medium in an executable format. In an embodiment, the hardware logic consists of electronic circuits that follow the rules of Boolean Logic, software that contain patterns of instructions, or any combination of both.

The design is also described in the general context of computing device executable instructions, such as applications etc. being executed by a computing device. Generally, programs include routines, objects, widgets, plug-ins, and other similar structures that perform particular tasks or implement particular abstract data types. Those skilled in the art can implement the description and/or figures herein as computer-executable instructions, which can be embodied on any form of computing machine-readable media discussed herein.

Some portions of the detailed descriptions herein are presented in terms of algorithms/routines and symbolic representations of operations on data bits within a computer memory. These algorithmic descriptions and representations are the means used by those skilled in the data processing arts to most effectively convey the substance of their work to others skilled in the art. An algorithm/routine is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms/routine of the application including the program modules may be written in a number of different software programming languages such as C, C++, Java, HTML, or other similar languages.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computing system, or similar electronic computing device, that manipulates and transforms data represented as physical (electronic) quantities within the computing system's registers and memories into other data similarly represented as physical quantities within the computing system memories or registers, or other such information storage, transmission or display devices.

Although embodiments of this design have been fully described with reference to the accompanying drawings, it is to be noted that various changes and modifications will become apparent to those skilled in the art. Such changes and modifications are to be understood as being included within the scope of embodiments of this design as defined by the appended claims. The invention is to be understood as not limited by the specific embodiments described herein, but only by scope of the appended claims.

What is claimed is:

1. A computer-implemented method, comprising:
   configuring a wearable electronic device to communicate at least one notification to an individual;
   monitoring content from a time synchronous application utilized by the individual, physical activity data associated with the individual, sleep activity data associated with the individual, and a state of mind of the individual;
   determining a correlation in the content based on the time synchronous application, the physical activity data, personal communication data, the sleep activity data, and the state of mind;
   determining whether to transmit the at least one notification to the individual, based on the correlation, whether a conflict exists, and whether the physical activity data, the sleep activity data, and the state of mind of the individual are below respective threshold levels over a predetermined period of time; and
   communicating the at least one notification to the individual through the wearable electronic device.

2. The computer-implemented method of claim 1, further comprising:
   setting at least one goal for the individual, based on the content and the correlation.

3. The computer-implemented method of claim 2, further comprising:
   adding an event to the time synchronous application, the event associated with the at least one goal when the at least one goal is not achieved by the individual within a predetermined period of time.

4. The computer-implemented method of claim 1, wherein the time synchronous application logs information in a time-based format, the information including at least one of: the personal communication data, information from a timeline application, or information from a calendar application.

5. The computer-implemented method of claim 4, wherein the personal communication data comprises at least one of: email data, social media data, or text message (SMS) data.

6. The computer-implemented method of claim 1, wherein the at least one notification communicates a suggestion to the individual regarding altering a pattern in at least one of: physical activity by the individual, sleep activity by the individual, or the state of mind of the individual.

7. The computer-implemented method of claim 1, further comprising:
   comparing, by an insight engine, the content against at least one historical average; and
   cross-referencing time synchronous application data from the time synchronous application to determine whether to transmit the at least one notification to the individual.

8. The computer-implemented method of claim 1, further comprising:
   configuring the wearable electronic device to present the at least one notification as at least one of: an audible notification, a vibration notification, or a visual notification.

9. The computer-implemented method of claim 1, wherein monitoring content from the state of mind further comprises configuring an interface to convey questions to the individual about a mood of the individual and receiving replies thereto.

10. The computer-implemented method of claim 1, wherein the content is obtained by pulling or receiving data from the wearable electronic device.

11. A computing system, comprising:
- at least one processor; and
- memory including instructions that, when executed by the at least one processor, cause the computing system to:
  - configure a wearable electronic device to communicate at least one notification to an individual;
  - monitor content from a time synchronous application utilized by the individual, physical activity data associated with the individual, sleep activity data associated with the individual, and a state of mind of the individual;
  - determine a correlation in the content based on the time synchronous application, the physical activity data, personal communication data, the sleep activity data, or the state of mind;
  - determine whether to transmit the at least one notification to the individual, based on the correlation, whether a conflict exists, and whether the physical activity data, the sleep activity data, and the state of mind of the individual are below respective threshold levels over a predetermined period of time; and
  - communicate the at least one notification to the individual through the wearable electronic device.

12. The computing system of claim 11, wherein the instructions, when executed by the at least one processor, further cause the computing system to:
- set at least one goal for the individual, based on the content and the correlation.

13. The computing system of claim 12, wherein the instructions, when executed by the at least one processor, further cause the computing system to:
- add an event to the time synchronous application, the event associated with the at least one goal when the at least one goal is not achieved by the individual within a predetermined period of time.

14. The computing system of claim 11, wherein the time synchronous application logs information in a time-based format, the information including at least one of: the personal communication data, information from a timeline application, or information from a calendar application.

15. The computing system of claim 14, wherein the personal communication data comprises at least one of: email data, social media data, or text message (SMS) data.

16. The computing system of claim 11, wherein the at least one notification communicates a suggestion to the individual regarding altering a pattern in at least one of: physical activity by the individual, sleep activity by the individual, or the state of mind of the individual.

17. The computing system of claim 11, wherein the instructions, when executed by the at least one processor, further cause the computing system to:
- compare, by an insight engine, the content against at least one historical average; and
- cross-reference time synchronous application data from the time synchronous application to determine whether to transmit the at least one notification to the individual.

18. The computer-implemented method of claim 11, wherein the instructions, when executed by the at least one processor, further cause the computing system to:
- configure the wearable electronic device to present the at least one notification as at least one of: an audible notification, a vibration notification, or a visual notification.

19. The computing system of claim 11, wherein monitoring content from the state of mind further comprises configuring an interface to convey questions to the individual about a mood of the individual and receiving replies thereto.

20. The computing system of claim 11, wherein the content is obtained by pulling or receiving data from the wearable electronic device.

* * * * *